United States Patent
Wang et al.

(10) Patent No.: US 12,345,706 B2
(45) Date of Patent: Jul. 1, 2025

(54) DETECTION KIT AND PREPARATION METHOD THEREOF AND A DETECTION METHOD FOR NOVEL CORONAVIRUS

(71) Applicant: BEIJING JINWOFU BIOENGINEERING TECHNOLOGY CO., LTD, Beijing (CN)

(72) Inventors: Li Wang, Beijing (CN); Lang Chen, Beijing (CN)

(73) Assignee: BEIJING JINWOFU BIOENGINEERING TECHNOLOGY CO., LTD, Beijing (CN)

(*) Notice: Subject to any disclaimer, the term of this patent is extended or adjusted under 35 U.S.C. 154(b) by 608 days.

(21) Appl. No.: 17/759,279

(22) PCT Filed: Sep. 22, 2021

(86) PCT No.: PCT/CN2021/119553
§ 371 (c)(1),
(2) Date: Jul. 21, 2022

(87) PCT Pub. No.: WO2022/068641
PCT Pub. Date: Apr. 7, 2022

(65) Prior Publication Data
US 2023/0077887 A1    Mar. 16, 2023

(30) Foreign Application Priority Data
Sep. 30, 2020 (CN) .......................... 202011069524.8

(51) Int. Cl.
*G01N 33/543* (2006.01)
*G01N 33/569* (2006.01)
(52) U.S. Cl.
CPC . *G01N 33/54388* (2021.08); *G01N 33/56983* (2013.01); *G01N 2333/165* (2013.01)
(58) Field of Classification Search
None
See application file for complete search history.

(56) References Cited

FOREIGN PATENT DOCUMENTS

| CN | 101650366 A | | 2/2010 |
|---|---|---|---|
| CN | 104991058 A | | 10/2015 |
| CN | 106290847 A | | 1/2017 |
| CN | 107132348 A | | 9/2017 |
| CN | 110658339 A | | 1/2020 |
| CN | 211 148 670 U | * | 7/2020 |
| CN | 111398583 A | | 7/2020 |
| CN | 111621597 A | | 9/2020 |
| CN | 112162092 A | | 1/2021 |
| WO | 2015044453 A1 | | 4/2015 |

OTHER PUBLICATIONS

Zhang et al. ("Establishing a high sensitivity detection method for SARS-CoV-2 IgM/IgG and developing a clinical application of this method"). Emerg Microbes Infect. Dec. 2020;9(1):2020-2029. doi: 10.1080/22221751.2020.1811161. PMID: 32799618; PMCID: PMC753433 (Year: 2020).*
International Search Report from PCT/CN2021/119553 Dec. 22, 2021, 3 pgs.

* cited by examiner

*Primary Examiner* — Jennifer Wecker
*Assistant Examiner* — Jonathan Bortoli

(57) ABSTRACT

The present disclosure discloses a detection kit and a preparation method thereof and a detection method for novel coronavirus, and relates to the technical field of biomedicine, including an antigen test strip. The antigen test strip includes a substrate, bibulous paper, immune nitrocellulose membrane, and immune microsphere pad. The immune microsphere pad, the immune nitrocellulose membrane and the bibulous paper are pasted on the substrate. The immune microsphere pad is coated with latex microsphere-labeled novel coronavirus SARS-CoV-2 monoclonal antibody 1. The immune nitrocellulose membrane is provided with a test line coated with novel coronavirus SARS-CoV-2 monoclonal antibody 2 and a quality control line coated with goat anti-mouse IgG polyclonal antibody. The present disclosure uses latex particles as labeled tracer, and uses antigen-antibody reaction and lateral chromatography to detect and analyze targets, having advantages of convenience and swift.

10 Claims, No Drawings

DETECTION KIT AND PREPARATION METHOD THEREOF AND A DETECTION METHOD FOR NOVEL CORONAVIRUS

CROSS REFERENCE TO RELATED APPLICATION

This application claims the benefit, under 35 U.S.C § 371 of international Application PCT/CN2021/119553, filed Sep. 22, 2021, which was published in accordance with PCT Article 21 on Apr. 7, 2022, and which claims the benefit of China patent application No. 202011069524.8, filed Sep. 30, 2020.

TECHNICAL FIELD

The present disclosure relates to the technical field of biomedicine and relates to a detection kit and a preparation method thereof and a detection method for novel coronavirus.

BACKGROUND ART

Since the end of 2019, Corona Virus Disease 2019 caused by infection of a novel coronavirus (SARS-CoV-2) has spread worldwide and has had a serious impact on health and economic development of all human beings, which is listed as a "public health emergency of international concern" by World Health Organization.

At present, the method for diagnosis of SARS-CoV-2 mainly adopts nucleic acid detection based on PCR reaction, combined with clinical symptoms and epidemiological data of patients. According to the current detection situation, nucleic acid detection tests need higher requirement for detection environment, operator experience and equipment. However, some backward areas or other grass-roots community hospitals lack laboratories with corresponding equipment and specialized staff. Therefore, in the process of eliminating a large number of suspected cases and timely controlling spread of pathogens, a rapid detection reagent is urgently needed to realize early diagnosis of latent infections and take relevant measures.

SUMMARY

The main purpose of the present disclosure is to overcome the defects existing in the prior art, as well as to provide a detection kit of novel coronavirus with low cost and relatively lower detection requirements. A preparation method of the detection kit and a detection method of novel coronavirus are disclosed in the present disclosure.

In order to achieve the above objective, a technical solution is provided by the present disclosure as follows:

A detection kit for novel coronavirus, including an antigen test strip; wherein the antigen test strip includes a substrate, a piece of bibulous paper, an immune nitrocellulose membrane, and an immune microsphere pad; and wherein the immune microsphere pad, the immune nitrocellulose membrane and the bibulous paper are pasted on the substrate lining; the immune microsphere pad is coated with novel coronavirus SARS-CoV-2 monoclonal antibody 1 labeled by latex microspheres; the immune nitrocellulose membrane is provided with a test line coated with novel coronavirus SARS-CoV-2 monoclonal antibody 2 and a quality control line coated with goat anti-mouse IgG polyclonal antibody.

In some embodiments, the latex microspheres are red latex microspheres with a diameter of about 300 nm.

The kit of the present disclosure is prepared by a following method comprising steps of:

(1) Preparation of an immune microsphere pad, comprising: labeling novel coronavirus SARS-CoV-2 monoclonal antibody 1 with latex microspheres to prepare an immune microsphere solution, and coating the immune microsphere solution on a release pad to prepare the immune microsphere pad;

(2) Preparation of an immune nitrocellulose membrane, comprising: preparing a test line solution by using novel coronavirus SARS-CoV-2 monoclonal antibody 2 and a quality control line solution by using a goat anti-mouse IgG polyclonal antibody, respectively, and coating the test line solution and the quality control line solution on the immune nitrocellulose membrane;

(3) Preparation of an antigen test strip, comprising: pasting the immune microsphere pad, the immune nitrocellulose membrane, and bibulous paper on a substrate to prepare a semi-finished plate of the antigen test strip; cutting the semi-finished plate of the antigen test strip to prepare antigen test strip.

Among them, a specific method for labeling the novel coronavirus SARS-CoV-2 monoclonal antibody 1 with latex microspheres is:

a. Pretreatment of a latex microsphere: washing the latex microsphere solution with labeling buffer MES;

b. Activation of EDC: adding the pretreated latex microsphere in step (a) to the labeling buffer MES, and then adding EDC and NHS solution to conduct mixing and reaction;

c. Latex labeling: centrifuging the reacted mixed solution, adding an obtained precipitates to MES buffer to reconstitute, and sonicating the reconstituted solution, then adding novel coronavirus SARS-CoV-2 monoclonal antibody 1 to react;

d. Blocking: adding an aminoethanol solution to conduct reaction and blocking; then centrifuging, discarding a supernatant to obtain a precipitate for later use;

e. Centrifugal purification: reconstituting the precipitate with TBS buffer, and sonicating the reconstituted solution to obtain the immune microsphere solution.

In some embodiments, a dose ratio of activator EDC is as follows: when concentration of the latex microsphere solution is 1% and dose of the latex microsphere solution is 500 µL, concentration of EDC solution is 100 mg/mL and dose of the EDC solution is 5 µL; that is, ratio of dose of EDC to quality of the latex microsphere is 100:1.

Dose ratio of the latex-labeled novel coronavirus SARS-CoV-2 monoclonal antibody 1 in step (c) is as follows: when concentration of the latex microsphere solution is 1% and dose of the latex microsphere solution is 500 µL, then dose of the novel coronavirus SARS-CoV-2 monoclonal antibody 1 is 1-2.5 mg/mL, preferably 2.0 mg/mL based on volume of the latex microsphere solution; that is, ratio of dose of the novel coronavirus SARS-CoV-2 monoclonal antibody 1 to quality of the latex microspheres is 2:1.

A reaction time of latex labeling in step (c) is 3-5 hours, preferably is 4 hours.

In preparation process of the immune microsphere pad in step (1), spray dose of the immune microsphere solution on the release pad is 2.5-3.0 µL/cm, and the immune microsphere pad obtained after spraying is dried at 38-42° C. for 4-16 hours; during preparation of the immune nitrocellulose membrane in step (2), the spray dose of the test line solution and the quality control line solution is each 2.0-2.5 mg/mL, and the prepared immune nitrocellulose membrane is dried at 38-42° C. for 4-16 hours.

The detection kit for novel coronavirus of the present disclosure further includes a sample extract solution, wherein the sample extract solution is prepared using 0.15M NaCl solution as base solution, and includes Triton-100 and NP-40; wherein concentration of Triton-100 in the sample extract solution is 0.5%, and concentration of NP-40 in the sample extract solution is 1%.

In the antigen/antibody detection, the principle of antigen-antibody immune response is applied to detect antibodies produced by human immune response induced by viral antigens and viral proteins.

In antibody detection, antibodies are principally detected through a specific immune reaction between antigen recombinant proteins and potential novel coronavirus antibodies in blood samples. After a virus infects human body, the antigenic determinants contact lymphocytes and induce lymphocytes to produce specific antibodies. Immune responses in different individuals have different strengths and reaction times, which will have a greater impact on sensitivity of antibody detection. Antigen detection is based on an immune reaction between specific antibodies and viral proteins in the sample, which allows direct detection of samples at infected sites.

In the present disclosure, latex particles are used as a labeled tracer, and antigen-antibody reaction and lateral flow assay are used to detect and analyze a target. It has advantages of convenience and quickness in practical operation: no testing expertise is required for testing personnel, no professional equipment configuration is required for testing experiments, and testing can be widely carried out in grass-roots community hospitals and health service centers.

The reason why latex particles are used as labeled tracers is that latex particles have uniform particle size, bright color, and can be coupled with functional groups on their surface. Therefore, covalent labeling can be used, and the labeled antibody is stable and not prone to detach, which is an ideal visually labeled tracer. Besides, the production process for latex particle has been well developed, and there are many high-quality latex particle suppliers in market, such as Thermo Fisher, Merck, Suzhou Vdo Biotech Co.ltd and other companies. The applicant purchased high-quality latex particles for immediate labeling operation. The obtained tracers provide good uniformity, a more controllable product coefficient of variation (CV) and small difference between batches.

DETAILED DESCRIPTION OF THE EMBODIMENTS

The present disclosure will be described in detail below with reference to specific embodiments.

The novel coronavirus (SARS-CoV-2) monoclonal antibodies 1 and 2 used in examples of the present disclosure are screened by the applicant:

Novel coronavirus (SARS-CoV-2) monoclonal antibody 1 is antibody strain 12B3, and novel coronavirus (SARS-CoV-2) monoclonal antibody 2 is antibody strain 105. Because S protein of novel coronavirus (SARS-CoV-2) is easily degraded, other specific antibodies against N protein of the novel coronavirus (SARS-CoV-2) are suitable to be used in the present disclosure.

The preliminary screening is carried out as follows: artificially synthetic antigens are coated on a 96-well plate at 100 µg/well, then a corresponding monoclonal antibody sample is added, the 96-well plate is put in a shaker at 37° C. for 30 min. After washing, a goat anti-mouse enzyme-labeled antibody (100 µg/well, 100 µL) is added at 37° C. and held for 30 min, then 200 µL of 1% BSA is added to each well for blocking. Washing is conducted after half an hour of the blocking, a chromogenic solution is added and then 50 µL of stop solution is added to terminate experiment, and cell lines corresponding to wells with an OD value above 2.0 are screened.

The secondary screening is the coating of the antibody. The screened antibody (1 µg/well) is coated on a 96-well plate, an artificially synthesized protein of N protein (100 µg/well, 100 µL/well) is added, and then a corresponding monoclonal antibody sample is added, the 96-well plate is put in a shaker at 37° C. for 30min. After washing, a goat anti-mouse enzyme-labeled antibody is added at 37° C. and held for 30min, then 200 µL of 1% BSA per well is added for blocking. Washing is conducted after half an hour of the blocking, chromogenic solution is added and then 50 µL of stop solution is added to terminate experiment. Cell lines corresponding to wells with an OD value above 1.0 are screened and cultured.

The matchable cell lines with higher OD values from the secondary screening are selected for cloning, and finally novel coronavirus (SARS-CoV-2) monoclonal antibody 1 (from antibody strain 12B3) and novel coronavirus (SARS-CoV-2) monoclonal antibody 2 (from antibody strain 105) are selected.

EXAMPLE 1

Screening of Labeled Tracers

In this example, colloidal gold and red latex microspheres were used as markers for comparison. The colloidal gold having a diameter of about 40 nm (chloroauric acid: trisodium citrate=1:1.1), and the red latex micro spheres having a diameter of about 300 nm were used.

1. Colloidal Gold Labeling Process:

1.5 mL of colloidal gold was taken and added to 40 µL of 0.1M $K_2CO_3$ to adjust pH of the colloidal gold to 7.0;

2. 100 µg of novel coronavirus (SARS-CoV-2) monoclonal antibody 1 was added, followed by standing for 45 minutes;

3. After centrifugalizing at 8000 r/min for 15 min, the supernatant was discarded;

4. Precipitates obtained from centrifugation were reconstituted with 5 mL of gold standard working solution, and the reconstituted solution was coated on glass fiber membrane SB08. After the glass fiber membrane SB08 was dried overnight, glass fiber membrane SB08 was used by forming a reagent strip A in combination with a nitrocellulose membrane coated with novel coronavirus (SARS-CoV-2) monoclonal antibody 2.

2. Latex Labeling Process:

(1). 500 µL of 1% latex microspheres was taken and centrifugation was conducted at 13000rpm for 20 min, the supernatant was discarded;

(2). The precipitates was reconstituted by adding 500 µL of MES (2-(N-Morpholino) ethanesulfonic acid, 4-Morpholineethanesulfonic acid monohydrate), and the resulting reconstituted solution was sonicated, then the resulting mixture was mixed with 5 µL of 150 mg/mL EDC N-(3-Dimethylaminopropyl)-N'-ethylcarbodiimide hydrochloride) and 35.5 µL of 10 mg/mL NHS (N-Hydroxysuccinimide) and subjected to a reaction for 1 hour under oscillation.

(3). After centrifugalizing at 13,000 rpm for 20 min, the supernatant was discarded; the precipitates were reconstituted by adding 500 μL of MES and sonicated; 0.5 mg of novel coronavirus (SARS-CoV-2) monoclonal antibody 1 was added to it until reached a batch volume, and reaction overnight;

(4). 15 μL of 1M aminoethanol was added, and was subjected to blocking reaction for 30 min; and the resulting reaction mixture was centrifugalized at 13000 rpm for 20 minutes, the supernatant was discarded;

(5). The precipitates obtained by centrifugation were reconstituted with 5 mL of TBS. After mixing by sonication, the reconstituted solution was coated on glass fiber membrane SB08. After drying overnight, the glass fiber membrane SB08 was used by forming the reagent strip B in combination with a nitrocellulose membrane coated with novel coronavirus (SARS-CoV-2) monoclonal antibody 2.

3. Comparison of Labels:

A sample extract solution of a novel coronavirus recombinant N protein with a standard concentration of 2.2 mg/mL was taken for serial dilution, and following results were obtained.

TABLE 1

Results of preference test for labeled tracers

| sample concentration (ng/mL) | 2.2 | 0.1 | 0.01 | 0.005 |
|---|---|---|---|---|
| A | + | + | − | − |
| B | + | + | + | ± |

It can be seen from the data in Table 1 that sensitivity of colloidal gold labeling and latex labeling was about 10 times different, so latex microspheres were selected as the labeled tracers herein.

EXAMPLE 2

Product Preparation Example

1) Novel coronavirus (SARS-CoV-2) monoclonal antibody 1 was labeled with latex microspheres to prepare an immune microsphere solution [latex microspheres-novel coronavirus (SARS-CoV-2) monoclonal antibody 1 complex].

2) The immune microsphere solution [latex microsphere-novel coronavirus (SARS-CoV-2) monoclonal antibody 1 complex] was diluted appropriately and was coated on a release pad to prepare an immune microsphere pad.

3) A test line (T line) solution was prepared with novel coronavirus (SARS-CoV-2) monoclonal antibody 2, and a quality control line (C line) solution was prepared with goat anti-mouse IgG.

4) C line and T line solutions were sprayed on a nitrocellulose membrane to prepare an immune nitrocellulose membrane.

5) The immune microsphere pad and the immune nitrocellulose membrane were dried.

6) The immune microsphere pad [coated with latex microspheres-novel coronavirus (SARS-CoV-2) monoclonal antibody 1 complex], the immune nitrocellulose membrane [coated with novel coronavirus (SARS-CoV-2) monoclonal antibody 2 and goat anti-mouse IgG] and the bibulous paper were pasted on a plastic substrate to form a semi-finished plate of antigen test strip of novel coronavirus (SARS-CoV-2).

7a) A piece of handle paper, MAX glue, etc. were pasted onto the semi-finished plate, and the semi-finished plate of antigen test strip of novel coronavirus (SARS-CoV-2) was cut into reagent strips, and was put into an aluminum foil bag together with desiccantThe reagent strips were sealed and packaged to obtain a single-person antigen test strip (strip type) of novel coronavirus (SARS-CoV-2).

7b). A semi-finished plate of antigen test strip of novel coronavirus (SARS-CoV-2) was cut into reagent strips, put into a slot of a plastic sheet, assembled into a card, and was put into an aluminum foil bag together with desiccant. After the card was sealed and packaged, an single-person antigen test strip (card form) of novel coronavirus (SARS-CoV-2) was obtained.

8) A certain number of the single-person antigen test strip of novel coronavirus (SARS-CoV-2), the sample extract solution, and the instruction for use were packed together to obtain a finished antigen detection kit (latex method) of novel coronavirus (SARS-CoV-2).

EXAMPLE 3

Process Parameters for Screening of Kit Preparation

1. Preparation Process of Immune Microsphere Solution

Steps of latex labeling were performed in accordance with relevant literature and instruction for use of manufacturer, and a principle of EDC activation labeling was used. Basic steps were as follows:

(1) Pretreatment of latex: A latex microsphere solution diluted to 1% was measured and a labeling buffer MES was added to the latex microsphere solution to a batch volume. Then resulting mixture was washed, centrifuged at 13,000 rpm for 20 min, and the supernatant obtained was discarded; MES was added to the precipitate to reconstitute the batch volume, sonicated, centrifuged at 13000 rpm for 20 min, and the supernatant was discarded;

(2) Activation of EDC: a certain volume of labeling buffer MES was added to the precipitates, and a certain volume of 15 mg/mL EDC (0.01 mL/mL, ratio of added volume of EDC to added volume of 1% of latex microsphere solution, an effect on system caused by volume change was avoided) and 10 mg/mL of NHS (0.075 mL/mL, ratio of added volume of NHS to added volume of 1% of latex microsphere solution, an effect on system caused by volume change was avoided) was mixed to a batch volume followed by reacting for 1 h. After centrifugalizing at 13,000 rpm for 20 min, the supernatant was discarded; MES was added to the precipitates to reconstitute in a certain volume of batch volume, and sonicated;

(3) Latex labeling: a certain amount of novel coronavirus (SARS-CoV-2) monoclonal antibody 1 was measured and added to a batch volume, and was allowed to react overnight;

(4) Blocking: 1M aminoethanol (0.03 mL/mL, ratio of volume of aminoethanol added to volume of 1% of latex microsphere solution, an effect on system caused by volume change was avoided) was added, followed by reacting for 30 min and blocking;

(5) Centrifugal purification: Centrifugalizing at 13,000 rpm for 20 min, a supernatant was discarded; TBS was added to a batch volume to reconstitute obtained precipitated particles, and sonicating the reconstitute solution in a rotator for 4 hours;

(6) Repetition of centrifugation: Centrifugalizing at 13000rpm for 20 min. A supernatant was discarded; TBS was added to a batch volume to reconstitute obtained precipitated particles, and ultrasonic blending for later use. The marking job was finished and an immune microsphere solution [novel coronavirus (SARS-CoV-2) monoclonal antibody 1-latex microsphere complex] was obtained.

Several important parameters in labeling process were: amount of EDC, concentration of labeled antibody and reaction time. Studies were conducted respectively and an optimum process was obtained.

1.1 Determination of amount of EDC:

EDC was used as an activator, and use of EDC at a too low concentration resulted in reduced labeling efficiency and unexpected sensitivity of products; and use of EDC at a too high concentration resulted in agglutination after latex labeling or increase non-specific reaction. Therefore, we optimized concentration of EDC in a certain amount of microspheres and a certain added volume of EDC (the concentration of the latex microsphere solution was 1% and the dose was 500 μL for experimental contrast).

TABLE 2

Test results for determination of EDC concentration

| Number | 1 | 2 | 3 | 4 |
|---|---|---|---|---|
| Amount of EDC (5 μL) | 20 mg/mL | 100 mg/mL | 150 mg/mL | 200 mg/mL |
| Novel coronavirus (SARS-CoV-2) monoclonal antibody 1 | 2 mg/mL | 2 mg/mL | 2 mg/mL | 2 mg/mL |
| Test results at minimum detection limit | − | + | + | ++ |
| Test results of positive samples (P1) | + | ++ | ++ | +++ |
| Test results of negative sample (N1) | − | − | ± | + |
| With or without agglutination after labeling | − | − | − | + |

Conclusion: When other conditions were fixed, sensitivity increased with an increase of EDC concentration, but a false positive reaction occurred when EDC concentration was above 150 mg/mL. However, an EDC concentration of 100 mg/mL showed good sensitivity and specificity, so it was determined that a consumption amount of EDC was that 5 μL of 100 mg/mL EDC was added to 1% of latex microsphere solution 500 μL. A mass ratio of microspheres and EDC under the optimal reaction conditions was 1:100.

1.2 Determination of Amount of Labeled Antibody

Amount of labeled antibody had a certain impact on performance of a product. Too low concentration led to low sensitivity, and too high concentration increased non-specific reactions easily. Therefore, we optimized amount of labeled antibody (concentration of latex microsphere solution was 1%, dosage was 500 μL, concentration of EDC was 100 mg/mL; and addition amount of EDC was 5 μL for experimental comparison).

TABLE 3

Test results for determination of labeled antibody amount

| Number | 1 | 2 | 3 | 4 |
|---|---|---|---|---|
| Novel coronavirus (SARS-CoV-2) monoclonal antibody 1 | 1 mg/mL | 1.5 mg/mL | 2 mg/mL | 2.5 mg/mL |
| Results at minimum detection limit | − | + | + | ++ |
| Test results of positive samples (P1) | + | + | ++ | +++ |
| Test results of negative sample (N1) | − | − | − | ± |

Conclusion: When other conditions were fixed, sensitivity increased with an increase of labeled antibody, but a slightly false positive reaction occurred when the labeled antibody was above 2.5 mg/mL. When the labeling amount was 1.5 mg/mL and 2.0 mg/mL, performances met requirements, but positive reaction intensity was slightly weaker when the labeling amount was 1.5 mg/mL, so the final amount of labeled antibody was 2.0 mg/mL, that was, 1 mg of novel coronavirus (SARS-CoV-2) monoclonal antibody 1 was added to 500 μL of 1% latex microspheres solution, and the mass ratio of novel coronavirus SARS-CoV-2 monoclonal antibody 1 to latex microspheres was 2:1.

2.3 Determination of Labeling Time

Reaction time had an impact on binding efficiency of antibody and latex, a shorter time led to lower labeling efficiency, and a longer time to a more sufficient labeling. Therefore, we confirmed the minimum reaction time required (A test was conducted using a previously determined dosage of latex microspheres, EDC, and Novel coronavirus SARS-CoV-2 monoclonal antibody 1).

TABLE 4

Test results of reaction time determination

| Number | 1 | 2 | 3 | 4 | 5 |
|---|---|---|---|---|---|
| reaction time | 1 h | 2 h | 3 h | 4 h | 5 h |
| Results at minimum detection limit | − | − | + | + | + |
| Test results of positive samples (P1) | ± | + | + | ++ | ++ |
| Test results of negative sample (N1) | − | − | − | − | − |

Conclusion: When other conditions were fixed, different reaction times had obvious influence on performance after labeling. It could be seen from above table that binding efficiency was very low when reaction time was less than 2 hours, a minimum detection limit could not be detected, and positive medium concentration test showed light-colored results. A period of 3 hours was the minimum required reaction time, and performance had been improved when extended to 4 hours. Beyond 4 hours, extension of time no longer had a big impact on product. Therefore, 4 hours was determined as the optimum time required for reaction.

2. Preparation Process of Immune Microsphere Pad 2.1 Determination of Optimal Spraying Amount of Immune Microsphere Dilution Solution Release pad had strong protein adsorption capacity and hydrophilicity, and a suitable concentration of immune microsphere solution was sprayed on the pad and dried to obtain a solid-phase protein. Too high or too low spraying volume in an immunochromatographic test could affect sensitivity, specificity, and uniformity of product. If the spraying volume was too high, it might cause some non-specific reactions and wasted antibodies; if the spray volume was too low, sensitivity of product might be reduced. During a spraying process of the release pad, if the spraying volume was too high, it was easily greater than an effective adsorption capacity of the release pad, then caused a deep background in detection process, the running plate was not clear, release was not clean and other phenomena for unjudged results. There were two purposes to determine the spraying amount: one was to ensure that immune reaction was fully carried out; the other was to save antibody protein as much as possible to avoid non-specific reactions and excessive waste.

Test method: An immune microsphere solution [latex microsphere-novel coronavirus (SARS-CoV-2) monoclonal antibody 1 complex] was diluted according to 1.0 μL/cm, 2.0 μL/cm, 2.5 μL/cm, 3 μL/cm, and 5 μL/cm gradient spraying volume. A parameter of 1 μL/cm was used for streaking, and after drying, test strips were assembled for performance testing to determine the optimal spraying amount. Test results are shown in Table 5 below.

TABLE 5

Test results of optimal spraying amount determination of immune microsphere pad

| | Spraying amount (μL/cm) | | | | |
| --- | --- | --- | --- | --- | --- |
| | 1.0 | 2.0 | 2.5 | 3.0 | 5.0 |
| Phenomenon description | Thin lines, uneven color, severe breakpoints | uneven line and color | uniform line and color | uniform line and color | Line color was extremely dark, red exudate in back of release pad |
| Results at minimum detection limit | − | − | + | + | ++ |
| Test results of positive samples (P1) | ± | + | + | ++ | +++ |
| Test results of negative sample (N1) | − | − | − | − | ± |

Note:
"+" means the color was light, "++" means the color was obvious, "+++" means the color was very dark, "−" means the color was invisible.

Test results showed that when the spraying volume was 1.0 μL/cm and 2.0 μL/cm, line color was light and uneven, and immune reaction was not sufficient; when the spraying volume was 2.5 μL/cm and 3 μL/cm, band color was uniform and easy to judge, the immune reaction was sufficient. According to a principle of no waste and reduction of non-specific reactions, the spraying volume of process was determined to be 2.5 μL/cm.

2.2 Determination of Optimal Drying Conditions for Immune Microsphere Pads

The drying conditions after the spray spot have an effect on the performance of the immune microsphere pad. Test showed that the immune microsphere pad after spraying could achieve good results when it was dried in an oven at 38-42° C. for more than 4 hours.

Test method: The immune microsphere pads after spraying was put into an oven at 38-42° C. to dry for 2 h, 3 h, 4 h, 8 h, 16 h and 18 h, respectively. After drying, test strips were assembled for appearance observation and performance testing. The best drying time was determined based on the appearance uniformity and eligibility in the performance testing. Test results are shown in Table 6 below.

TABLE 6

Test results of optimal drying time for immune microsphere pads

| Drying time | 2 h | 3 h | 4 h | 8 h | 16 h | 18 h |
| --- | --- | --- | --- | --- | --- | --- |
| Appearance characters | background was red | background was red | eligible | eligible | eligible | eligible |
| Performance testing | false positive | eligible | eligible | eligible | eligible | false negative |

Test results showed that when the drying time was less than 4 h, background of the immune microsphere pad was relatively red during testing, and false positive results appeared; when the drying time was more than 16 h, there were false negatives appeared in test results; when the drying time was 4 to 16 h, background of the immune microsphere pad was clean, and the performance testing were all eligible.

Therefore, the optimal drying time of the immune microsphere pad was determined to 4-16 hours.

3. Preparation Process of Immune Nitrocellulose Membrane 3.1 Determination of Optimal Coating Concentration of Antibody Protein on Immune Nitrocellulose Membrane There were two protein-coated bands on the immune nitrocellulose membrane, namely quality control line (C line) and the test line (T line). The C line was coated with goat anti-mouse IgG antibody, and the T line was coated with novel coronavirus (SARS-CoV-2) monoclonal antibody 2.

There were two purposes to determine coating concentration of C/T line: one was to ensure that immune reaction was fully carried out; the other was to save antibody protein as much as possible to avoid non-specific reactions and excessive waste.

Test method: Goat anti-mouse IgG antibody and novel coronavirus (SARS-CoV-2) monoclonal antibody 2 were diluted to 1.0 mg/mL, 1.5 mg/mL, 2.0 mg/mL and 2.5 mg/mL, respectively. A parameter of 1 μl/cm was used for streaking. After drying, test strips were assembled for performance testing. Color intensity and uniformity of the C/T line was observed to determine an appropriate coating concentration. Test results are shown in Table 7 below:

TABLE 7

Test results for determination of the optimal coating concentration of antibody protein on immunonitrocellulose membranes

| | Coating concentration (mg/mL) | | | |
| --- | --- | --- | --- | --- |
| | 1.0 | 1.5 | 2.0 | 2.5 |
| Color intensity of C line | ± | ++ | +++ | +++ |
| Color intensity of T line | ± | + | ++ | ++ |
| Phenomenon description | Uneven line and color | Even line and color | Even line and color | Even line and color |

Note:
"+" means the color was light, "++" means the color was obvious, "+++" means the color was very dark, "−" means the color was invisible.

Test results showed that when the coating concentration was 1.0 mg/mL, the color of the C/T line is relatively light and uneven, which affected interpretation of the results; when the coating concentration was 1.5 mg/mL, the color of the C line was obvious, but the color of the T line was light indicated immune reaction was insufficient; when the coating concentration was 2.0 mg/mL and 2.5 mg/mL, a band color of the C line and the T line was easy to judge, and uniform band color indicated sufficient immune reaction. According to a principle of no wasting and reduced non-specific reactions, the coating concentration of protein in C line and T line in the streaking process was determined to be 2.0 mg/mL.

3.2 Determination of Optimal Drying Conditions for Immune Nitrocellulose Membranes Drying conditions after streaking had an effect on performance of immune nitrocellulose membranes. Test showed that the immune nitrocellulose membrane after streaking could achieve good results when it was dried in an oven at 38-42° C. for more than 4 hours.

Test method: The nitrocellulose membrane after streaking was put in an oven at 38-42° C. to dry for 2 h, 3 h, 4 h, 8 h, 16 h and 18 h, respectively. After drying, test strips were assembled for appearance observation and performance testing, and the best drying time was determined based on C/T line uniformity and eligibility in the performance testing. Test results are shown in Table 8 below:

TABLE 8

Test results of optimal drying time for immune nitrocellulose membrane

| Drying time | 2 h | 3 h | 4 h | 8 h | 16 h | 18 h |
| --- | --- | --- | --- | --- | --- | --- |
| Appearance Characters | Discrete and tailed | Discrete and tailed | eligible | eligible | eligible | eligible |
| Performance Testing | eligible | eligible | eligible | eligible | eligible | false negative |

Test results showed that when the drying time was less than 4 h, C/T line had a tail and edges of the lines were uneven and dispersed; when the drying time was more than 16 h, false negatives appeared in the test results; when the drying time was 4 to 16 h, the C/T line was neat without tailing, and performance test was all eligible.

Therefore, the optimal drying time of immune nitrocellulose membrane was determined to be 4-16 h.

4. Preparation Process of Sample Extract 4.1 Materials 0.15M NaCl, Triton-100, NP-40.

4.2 Preparation Method 0.15M NaCl was used as a base solution, concentrations of Triton-100 and NP-40 were screened respectively, so as to screen for the best formula for sample extract solution to ensure suitability of reagent card reaction system.

Extract solution of Triton-100 with concentrations of 0.1%, 0.5%, 1%, 1.5% and 2% were prepared respectively; extract solution of NP-40 with concentrations of 0.1%, 0.25%, 0.5%, 0.75% and 1% were prepared respectively. The lowest detection limit reference materials S1 and negative throat brush samples were taken for testing, the extract solution of the two formulas was tested by adding samples, respectively, and the test results and phenomena were recorded.

4.3 Results 4.3.1 Experimental Results of Different Concentrations of Triton-100

1) Test results of the lowest detection limit reference material P1

TABLE 9

Test results of minimum detection limit reference material P1

| Concentration | 0.1% | 0.5% | 1% | 1.5% | 2% |
|---|---|---|---|---|---|
| C line | +++ | +++ | +++ | +++ | +++ |
| T line | | + | ++ | +++ | +++ |
| Phenomenon observation | negative | weakly positive | normal | strongly positive | strongly positive |

2) Test results of negative throat swab samples

TABLE 10

Test results of negative throat swab samples

| concentration | 0.1% | 0.5% | 1% | 1.5% | 2% |
|---|---|---|---|---|---|
| C line | +++ | +++ | +++ | +++ | +++ |
| T line | − | − | − | + | ++ |
| Phenomenon observation | negative | negative | negative | false positive | false positive |

Test results showed that the optimal concentration of Triton-100 was 1%.

4.3.2 Experimental Results of Different Concentrations of NP-40

TABLE 11

Experimental results of different concentrations of NP-40

| | Tested concentration of positive reference material P1 | | | | |
|---|---|---|---|---|---|
| | 0.1% | 0.25% | 0.5% | 0.75% | 1% |
| C line | +++ | +++ | +++ | +++ | +++ |
| T line | +++ | +++ | ++ | + | − |
| Phenomenon observation | strongly positive | strongly positive | normal | weakly positive | negative |

2) Test results of negative throat swab samples

TABLE 12

Test results of negative throat swab samples

| Concentration | 0.1% | 0.25% | 0.5% | 0.75% | 1% |
|---|---|---|---|---|---|
| C line | +++ | +++ | +++ | +++ | +++ |
| T line | + | + | − | − | + |
| Phenomenon observation | false positive | false positive | normal | negative | false positive |

Test results showed that the optimal concentration of NP-40 was 0.5%.

4.3.3 Validation of Two Optimal Component Combinations

Extract solutions were prepared with 0.15M NaCl, 1% Triton-100, 0.5% NP-40 as a combination, and the minimum detection limit reference material Si and 10 negative throat swab samples were tested in parallel for 5 times. Results are shown as follows.

1) Test results of minimum detection limit reference material S1:

TABLE 13

Test results of minimum detection limit reference material S1

| Times | 1 | 2 | 3 | 4 | 5 |
|---|---|---|---|---|---|
| C line | +++ | +++ | +++ | +++ | +++ |
| T line | ++ | ++ | ++ | ++ | ++ |
| Phenomenon observation | normal | normal | normal | normal | normal |

2) Test results of negative swab samples:

TABLE 14

Test results of negative swab sample

| Sample number | 1# | 2# | 3# | 4# | 5# |
|---|---|---|---|---|---|
| C line | +++ | +++ | +++ | +++ | +++ |
| T line | − | − | − | − | − |
| Phenomenon observation | normal | normal | normal | normal | normal |
| Sample number | 6# | 7# | 8# | 9# | 10# |
| C line | +++ | +++ | +++ | +++ | +++ |
| T line | − | − | − | − | − |
| Phenomenon observation | normal | normal | normal | normal | normal |

Test results showed that concentration of 1% Triton-100 and concentration of 0.5% NP-40 was were the best combination for extract solution.

EXAMPLE 4

Novel Coronavirus Detection Process

1. Detection of Reaction System Conditions and Determination Basis

1. Sample Volume

1) A suitable sample type for test kit herein was throat swab.

2) Throat swabs were obtained by standard methods in clinical laboratories: 2 plastic rod swabs with polypropylene fiber tips/synthetic flocking tips were used to wipe bilateral pharyngeal tonsils and posterior pharyngeal wall at the same time. Swabs should be treated as soon as possible after sampling. Specimens that could be detected within 24 hours could be stored at 4° C.; those could not be detected within 24 hours should be stored at −70° C. or below (if −70° C. storage condition was not available, the specimens could be temporarily stored in a −20° C. refrigerator).

Specimens that had grown bacteria, had been stored for too long, or had been repeatedly frozen and thawed should not be used to avoid non-specific reactions caused by sample contamination or bacterial growth.

3) Samples must be returned to room temperature before testing.

2. Determination of Sample Volume and Sample Solution Volume

Test method: 1 drop, 2 drops, 3 drops, and 4 drops of positive reference material pl were added to wells respectively, and test results and phenomena were recorded. The test results are shown in Table 15:

TABLE 15

Test results when the sample volume was 1 drop

| | Adding amount | | | | |
|---|---|---|---|---|---|
| | 1 drop | 2 drops | 3 drops | 4 drops | 5 drops |
| C line | / | +++ | +++ | +++ | +++ |
| T line | / | ++ | ++ | ++ | + |
| Phenomenon observation | Incomplete chromatography | Normal chromatography | Normal chromatography | Normal chromatography with a little liquid residue in wells | Occur overflow |

Note:
"+" indicated weak bands, "++" indicated obvious bands, "+++" indicated very dark bands, and "/" indicated invisible bands.

Test results: When adding amount of sample extract solution was 1 drop, chromatography of product was incomplete, which affected interpretation; when adding amounts of sample extracts was 5 drops, and a phenomenon of overflow appeared, which affected the chromatography. Therefore, an adding amount of 2-3 drops of sample extract solution not only avoided that the adding amount was too little to affect effect of chromatographic, but also avoided that the adding amount was too much to cause overflow.

3. Reaction Conditions of System 3.1 Reaction Conditions 3.1.1 Influence of Humidity Environment on Product Testing This product involved a latex microsphere immune chromatographic reaction, and could cause product failure after got damp.

Test method: Card-type and strip-type products were disassembled from aluminum foil bags and placed in a room temperature environment having a humidity of 40%, 50%, 60%, 70%, 80% and 90%, respectively, and positive and negative samples that had been identified were used for testing, and the test was conducted every hour and the test results were recorded.

The test results are shown in Table 16 and Table 17 below.

TABLE 16

Test results of product under different humidity (card type)

| Test time (H) | 0 | 1 | 2 | 3 | 4 | 5 | 6 | 7 | 8 | 9 |
|---|---|---|---|---|---|---|---|---|---|---|
| 40% humidity | √ | √ | √ | √ | √ | √ | √ | √ | √ | √ |
| 50% humidity | √ | √ | √ | √ | √ | √ | √ | √ | √ | √ |
| 60% humidity | √ | √ | √ | √ | √ | √ | √ | √ | √ | x |
| 70% humidity | √ | √ | √ | √ | √ | √ | √ | x | x | x |
| 80% humidity | √ | √ | √ | √ | √ | x | x | x | x | x |
| 90% humidity | √ | √ | √ | x | x | x | x | x | x | x |

Note:
"√" indicated that the test result was the same as identification result, and "x" indicated that the test result was abnormal.

TABLE 17

Test results of product under different humidity (strip type)

| Test time (H) | 0 | 1 | 2 | 3 | 4 | 5 | 6 | 7 | 8 | 9 |
|---|---|---|---|---|---|---|---|---|---|---|
| 40% humidity | √ | √ | √ | √ | √ | √ | √ | √ | √ | √ |
| 50% humidity | √ | √ | √ | √ | √ | √ | √ | √ | √ | √ |
| 60% humidity | √ | √ | √ | √ | √ | √ | √ | √ | √ | x |
| 70% humidity | √ | √ | √ | √ | √ | √ | √ | x | x | x |
| 80% humidity | √ | √ | √ | √ | √ | x | x | x | x | x |
| 90% humidity | √ | √ | √ | x | x | x | x | x | x | x |

Note:
"√" indicated that the test result was the same as identification result, and "x" indicated that the test result was abnormal.

The test results showed that card-type and strip-type products had the same performance. In a room temperature environment of 40%-60% humidity, this product was stable up to 8 hours; in a room temperature environment of 70% humidity, it was stable up to 6 hours; in a room temperature environment of 80% humidity, it was stable up to 4 hours, and in a room temperature environment of 90% humidity, it was stable up to 2 hours in a room temperature environment. If test time longer than above specified time, chromatography speed was obviously reduced, and some products were difficult for chromatography.

Therefore, under normal indoor environment conditions, there were special requirements for humidity for the product herein, but prolonged exposure in a high-humidity environment should be avoided and the product should be used as soon as possible after the aluminum foil bag was opened.

3.1.2 Influence of Temperature Environment on Product Testing

The product disclosed herein involved an immune reaction which imposed no special requirement for reaction temperature. The reaction could start as long as samples to be tested was liquid, Besides, the product herein was generally used indoors, and a room temperature conditions could also meet the requirements of reaction temperature of product herein.

In order to better verify reaction temperature requirements of product herein, the lower and upper limits of storage temperature of product herein were designed as the upper and lower limits of the reaction temperature.

In order to determine the optimum reaction temperature, the lowest detection limit material S1 and samples were used for strip and card products at different experimental temperatures of 2-8° C., 16° C., 25° C., 30° C., 37° C., and 45° C., respectively. Detection method of an instruction manual was used for detection, and results were observed within 10-20 min. Sensitivity and specificity of test strips were mainly investigated, followed by concentration and clarity of bands and migration speed of samples.

Test results are shown in Table 18 and Table 19 below.

TABLE 18

Test results of products at different temperatures (card type)

| Temperature condition | Negative reference material N1 | | | Minimum detection limit reference material | | | |
|---|---|---|---|---|---|---|---|
| 4  | − | − | − | + | +  | −  | +  |
| 16 | − | − | − | + | +  | +  | +  |
| 25 | − | − | − | + | +  | +  | +  |
| 30 | − | − | − | + | +  | +  | +  |
| 37 | − | − | − | + | ++ | +  | +  |
| 40 | − | − | − | + | +  | +  | ++ |
| 45 | − | − | − | + | +  | ++ | ++ |

Note:
"+" means the test result was positive, "−" means the test result was negative.

TABLE 19

Test results of products at different temperatures (strip type)

| Temperature condition | Negative reference material N1 | | | Minimum detection limit reference material | | | |
|---|---|---|---|---|---|---|---|
| 4  | − | − | − | + | +  | −  | +  |
| 16 | − | − | − | + | +  | +  | +  |
| 25 | − | − | − | + | +  | +  | +  |
| 30 | − | − | − | + | +  | +  | +  |
| 37 | − | − | − | + | ++ | +  | +  |
| 40 | − | − | − | + | +  | +  | ++ |
| 45 | − | − | − | + | +  | ++ | ++ |

Note:
"+" means the test result was positive, "−" means the test result was negative.

The test results showed that color band became lighter at 2-8° C., and the color band was concentrated, but a migration speed of sample was slightly reduced; the test sample had a higher migration speed at a temperature above 37° C., and color bands diffused slightly, and the color became darker. In contrast, tests at 16° C., 25° C., and 30° C. were normal.

Therefore, we chose the best experimental temperature of 15-30° C.

3.2 Effective Judgment Time

For a kit, the higher the concentration of the test substance and the longer the reaction time, the more obvious the color development result would be. Both the antigen-antibody reaction and the completion of the chromatography of sample and marker needed a certain amount of time, so a minimum waiting time was required. At the same time, excessively long time might increase false positive reactions, and might also lead to sample backflow. When backflow occurred, false positive results generally appeared. Therefore, an additional highest time point must be set, so a time period for interpretation was generally set for the kits.

Test method: A positive reference material and a negative reference material were taken, a card type was tested according to instruction for use, and the test results and phenomena were recorded.

Test results: 5 minutes after the samples and extract solution were loaded, an immune reaction was complete, and C/T line was normal and clear; all samples were chromatographed to a water-absorbing end; a membrane background was completely washed away, and there was no color tailing phenomenon. Properly prolonging a reaction time could help to eliminate the background, make color of the membrane clearer and facilitate results determination. There was no non-specific reaction in multiple test results of positive and negative samples within 10 min, and the test results were correct.

Therefore, interpreting the test results within 10-20 min could not only ensure correctness of test results, but also ensure clean and clear membrane background.

2. Requirements for tested samples.

In the products in the present disclosure, throat swabs were used as tested samples, and collection of samples should comply with clinical sampling specifications.

1. Collection and treatment of throat swabs:

Samples should be collected from tonsils or posterior wall of throat using a sterile swab, avoiding touching teeth, gums, tongue, and inner surfaces of cheek. Swabs should be treated as soon as possible after sample collection. Swabs could be stored for 24 hours at room temperature or at 2-4° C. The temperature of the swabs and the kits should be returned to room temperature before testing.

Specimens that had grown bacteria, had been stored for too long, or had been repeatedly frozen and thawed could not be used to avoid non-specific reactions caused by sample contamination or bacterial growth. Samples must be brought to room temperature before testing.

2. Sample Volume

Too much sample volume of chromatographic reagents could easily lead to overflow, and samples directly flow to detection area without chromatography, which affects test results; at the same time, excessively small sample volume might cause samples to not to be successfully chromatographed to the detection area, and the test was unsuccessful. Therefore, sample volume should be strictly controlled during testing and operation should be carried out in accordance with requirements of instructions.

Throat swab sample: Cotton swab with throat swab samples was collected and inserted into a sample treatment tube, 300 μL of sample extract solution were added into the tube. The sample treatment tube was squeezed for 2 min, the cotton swab of sampling was rotated, and the sample was shaken well. After standing for 5 min, 2 to 3 drops of sample treatment solution were added dropwise.

3. Reagent Dosage

1. Preparation of Immune Microsphere Pads (1) Calculation benchmark: The basic scale was to treat 2.5 μL/cm of purified immune microsphere dilution solution.

Preparation of immune microsphere dilution solution: 30 mL of purified immune microsphere solution (latex microsphere-mouse anti-human IgM monoclonal antibody complex) was measured and diluted 10 times with 0.01M phosphate buffer (containing 0.01% BSA) of pH 7.8 to a total volume of 300 mL to prepare immune microsphere dilution solution.

(2) Preparation amount: Purified immune latex pad was calculated and measured according to length of release pad to be sprayed;

(3) All prepared and diluted immune latex dilution solutions were put in a corresponding position of a membrane-scribing and gold-spraying machine (to avoid air bubbles), the release pad was placed in a corresponding position on the running platform, and required programs for spraying membrane were selected and parameters were set according to product process requirements: every 2.5 μL of the immune latex dilution solution was sprayed onto a 1 cm release pad.

(4) Step (3) was repeated until all release pads were treated;

(5) The sprayed release pad was dried in an oven at 38-42° C. for more than 4 hours immediately, and sealed for later use;

(6) The dried immune microsphere pad was cut into 300 mm×7 mm strips;

(7) The strips were packaged in an aluminum foil bag containing desiccant, sealed and stored;

2. Preparation Process of Immune Nitrocellulose Membrane 2.1 Preparation of C-line Coating Solution Based on the needed amount of C-line solution to be prepared and the concentration of goat anti-mouse IgG antibody, the goat anti-mouse IgG stock solution was calculated and measured, and the original antibody solution was diluted with 0.01M phosphate buffer of pH7.8 to a final protein concentration of 2.0mg/ mL.

2.2 Preparation of T-Line Coating Solution

Based on the needed amount of T-line solution to be prepared and the concentration of the novel coronavirus (SARS-CoV-2) monoclonal antibody 2 stock solution, the novel coronavirus (SARS-CoV-2) monoclonal antibody 2 solution was calculated and measured, and diluted with 0.01M phosphate buffer of pH 7.8 to a protein concentration of 2.0 mg/mL.

2.3 Spot Immune Nitrocellulose Membrane (1) A membrane-dotting machine was cleaned according to an operation rules thereof.

(2) The membrane-dotting machine was debugged, inlet and outlet pipelines were connected, and C and T lines were put into C and T line solutions respectively.

(3) The spray speed and film running speed of the system were adjusted so that 1μl of C and T line coating solutions could be sprayed on each 1 cm length of the membrane zone.

(4) Nitrocellulose membrane was attached to the plastic substrate and a membrane dotting operation was conducted.

(5) The sprayed film was put into an oven at 38-42° C. and dried for more than 4 hours and sealed for later use.

3. Assembly and Inner Packaging Process (1) A work area was cleaned and an immune nitrocellulose membrane, an immune microsphere pad and other raw materials were prepared.

(2) The immune nitrocellulose membrane was pasted on middle of the plastic substrate, a piece of bibulous paper was pasted on the bibulous paper end of the plastic substrate, covered downward on the pasted nitrocellulose membrane, and pressed back and forth with hands.

(3) A piece of paper on the other side of the plastic substrate was torn off, the immune microsphere pad was pasted on the nitrocellulose membrane, and then the sample pad was pasted on the immune microsphere pad, pressed back and forth with hands, and assembled into a semi-finished plate.

(4) The pasted semi-finished plate should be inspected by a specially-assigned person. The bibulous paper should be pasted on the upper end of the membrane, covering the membrane with a length of 1.5 mm to 2 mm. The immune microsphere pad should be pasted below the membrane, covering a length of 1.5 mm to 2 mm; and the sample pad was pasted on the immune microsphere pad, covering a length of 1 mm to 1.5 mm.

(5) a. A piece of handle paper, MAX glue were pasted onto the semi-finished plate, parameters of a cutter was adjusted, the semi-finished plate was cut into reagent strips with the same specifications and sizes, and was put into an aluminum foil bag together with desiccant. After sealing and packing, a single-person antigen test strip (strip type) of novel coronavirus (SARS-CoV-2) was obtained.

b. The semi-finished plate was cut into reagent strips, put into a plastic card slot, and was put into aluminum foil bags together with desiccant, sealed and packaged to obtain a single-person antigen test strip (strip type) of novel coronavirus (SARS-CoV-2).

4. Outer Packaging Process (1) Several single-person antigen test strips (strip type) of novel coronavirus (SARS-CoV-2), sample extract solution, instruction for use, and so on, were put into a packaging box to prepare a finished antigen detection kit (latex method) of novel coronavirus (SARS-CoV-2).

(2) Sampling for inspection: random sampling was carried out in accordance with quality standard of antigen detection kit (latex method) of novel coronavirus (SARS-CoV-2) and a number of tests specified in the inspection operating procedures, then the samples were sent to quality department for inspection.

4. Method for Determining Effectiveness of System

1. After production process and reaction system were determined, a finished product was prepared for performance test to verify the production process and effectiveness of the reaction system.

2. Test method: According to the determined production process, immune microsphere pads and immune nitrocellulose membranes were prepared, assembled and packaged. Then performance test according to a determined reaction condition of the reaction system was performed, and test results were recorded. The test results are shown in Table 20 below.

TABLE 20

Validation results of production process and reaction system

| Test items | Test results | | | | | |
|---|---|---|---|---|---|---|
| | Number of testing | Number of positive result | Number of negative result | Color uniformity | Eligibilty | |
| Minimum detection limit | 3 | 3 | 0 | uniform | ☒ pass | ☐ fail |
| Positive coincident rate | 5 | 5 | 0 | / | ☒ pass | ☐ fail |
| Negative coincident rate | 5 | 0 | 5 | / | ☒ pass | ☐ fail |
| Reapeatability | 10 | 10 | 0 | uniform | ☒ pass | ☐ fail |

3. Test results: the minimum detection limit, positive coincidence rate, negative coincidence rate and repeatability tests all met requirements.

4. Conclusion: The above-determined production process and reaction system could meet the requirement of intended use of product herein.

Although the above embodiments have made a detailed description of the present disclosure, they are only a part of the embodiments of the present disclosure, not all embodiments. /The person skilled in the art can also obtain other embodiments according to the present embodiments without making creative efforts, and these embodiments should be regarded as falling within the claimed scope of the present disclosure.

What is claimed is:

1. A method of making a single-person antigen test strip card, comprising:
   a plastic substrate;
   a bibulous paper;
   an immune nitrocellulose membrane; and
   an immune microsphere pad; wherein the immune microsphere pad, the immune nitrocellulose membrane and the bibulous paper are disposed on the plastic substrate; the immune microsphere pad comprises severe respiratory syndrome coronavirus 2 (SARS-CoV-2) monoclonal antibody 1 including latex microspheres; the immune nitrocellulose membrane includes a test line and a quality control line, the test line comprising severe respiratory syndrome coronavirus (SARS-CoV-2) monoclonal antibody 2 and the quality control line comprising goat anti-mouse immunoglobulin G polyclonal antibody wherein the method comprises:
   A) preparing a first solution comprising immune microspheres by labeling an amount of severe respiratory syndrome coronavirus (SARS-CoV-2) monoclonal antibody 1 using an amount of latex microspheres;
   B) preparing the immune microsphere pad by diluting the first solution and coating a release pad using the diluted first solution;
   C) preparing a second solution comprising severe respiratory syndrome coronavirus (SARS-CoV-2) monoclonal antibody 2, and preparing a third solution comprising goat anti-mouse immunoglobulin G;
   D) preparing the immune nitrocellulose membrane by spraying the third solution onto the quality control line and by spraying the second solution onto the test line;
   E) drying the immune microsphere pad and drying the immune nitrocellulose membrane;
   F) forming a plate by pasting the immune microsphere pad, the immune nitrocellulose membrane and the bibulous paper onto the plastic substrate; and
   G obtaining the single-person antigen test trip card by pasting a piece of handle paper and polyurethane glue on the plate, cutting the plate into two or more reagent strips, assembling the two or more reagent strips into a card, putting the assembled card and a desiccant into an aluminum foil bag, and sealing the aluminum foil bag.

2. The method according to claim 1, wherein the latex microspheres are red latex microspheres having a diameter between 290 and 300 nm.

3. The method according to claim 1, wherein the amount of severe respiratory coronavirus (SARS-CoV-2) monoclonal antibody 1 to the amount of latex microspheres in step (A) is a 2:1 mass ratio.

4. The method according to claim 1, wherein the severe respiratory syndrome coronavirus 2 (SARS-CoV-2) monoclonal antibody 1 comprises a 12B3 antibody strain; and the severe respiratory syndrome coronavirus 2 (SARS-CoV-2) monoclonal antibody 2 comprises an a 1C5 antibody strain.

5. A kit for detecting novel coronavirus comprising the single person antigen test strip card of claim 1.

6. The kit according to claim 5 comprising a sample extract solution comprising sodium chloride, 2-[4-(2,4,4-trimethylpentan-2-yl)phenoxy]ethanol and polyethylene glycol nonyl phenyl ether and having a molarity of 0.15 moles of sodium chloride per liter of sample extract solution, a concentration of 0.5% 2-[4-(2,4,4-trimethylpentan-2-yl)phenoxy]ethanol (m/v), and a concentration of 1% polyethylene glycol nonyl phenyl ether (m/v).

7. The method according to claim 1 further comprising:
   H) treating the latex microsphere by washing the latex microspheres using a forth solution comprising a labeling buffer comprising (2-(N-morpholino)ethanesulfonic acid) (MES);
   I) activating an amount of 1-ethyl-3-(3-dimethylaminopropyl)carbodiimide (EDC) by adding the latex microspheres treated in step (H) to the forth solution, and obtaining a sixth solution by mixing the forth solution and a fifth solution comprising (N-hydroxy succinimide) (NHS) by adding the activated 1-ethyl-3-(3-dimethylaminopropyl)carbodiimide (EDC) and the fifth solution comprising (N-hydroxy succinimide) (NHS);
   J) latex labeling by centrifuging the reacted mixed solution, collecting obtained precipitates and reconstitution a seventh solution by adding MES buffer to the precipitates, sonicating the seventh solution, and reacting by adding SARS-CoV-2 monoclonal antibody 1; blocking by adding an aminoethanol solution; centrifuging a resulting reaction mixture, obtaining precipitates by discarding a supernatant; obtaining the labeled immune solution by centrifugating, reconstituting the precipitates with a tris-buffered saline TBS buffer, and sonicating a reconstituted solution.

8. The method according to claim 7, wherein the amount of 1-ethyl-3-(3-dimethylaminopropyl)carbodiimide (EDC) to the amount of latex microspheres is a 100 to 1 mass ratio.

9. The method according to claim 7 wherein the latex labeling in step is performed in a period of time of 4 hours.

10. The method according to claim 1, wherein the drying the immune microsphere pads in step (E) is performed at a temperature between 38 and 42° C. for a period of time between 4 and 16 hours; wherein the and the drying the nitrocellulose membrane is performed at a temperature between 38 and 42° C. for a period of time between 4 and 16 hours.

* * * * *